United States Patent [19]

Goldhaber

[11] 4,256,743
[45] Mar. 17, 1981

[54] INHIBITION OF BONE RESORPTION WITH $H_1$-BLOCKING ANTIHISTAMINES

[75] Inventor: Paul Goldhaber, Waban, Mass.

[73] Assignee: President and Fellows of Harvard College, Cambridge, Mass.

[21] Appl. No.: 88,397

[22] Filed: Oct. 26, 1979

Related U.S. Application Data

[63] Continuation-in-part of Ser. No. 14,070, Feb. 22, 1979, abandoned.

[51] Int. Cl.³ ............... A61K 31/44; A61K 31/54; A61K 31/13
[52] U.S. Cl. ............................. 424/247; 424/263; 424/325
[58] Field of Search ............ 424/263, 246, 247, 325

[56] References Cited

U.S. PATENT DOCUMENTS

| | | | |
|---|---|---|---|
| 3,070,503 | 12/1962 | Siegel et al. | 424/263 |
| 3,637,660 | 1/1972 | Erikson et al. | 424/246 |
| 3,726,976 | 4/1973 | Glasser | 424/263 |
| 3,894,151 | 7/1975 | Black et al. | 424/263 |
| 3,920,822 | 11/1975 | Durant et al. | 424/263 |
| 3,932,644 | 1/1976 | Durant et al. | 424/263 |
| 3,975,530 | 8/1976 | Durant et al. | 424/263 |

OTHER PUBLICATIONS

Inter. Symp. on Osteoporosis–1st–N.Y. (1969)–Osteoporosis (1970)–pp. 174–186, Raisz.
Clin. Exp. Immunol. (1978) 33, 166–173–Wennstrom et al.
J. Dent. Res. 45, 490–499 (1966)–Goldhaber.
J. Dent. Res. 50, 278–285 (1971)–Goldhaber.
57th Amer. Meeting Int. Assoc. Dent. Res. Prog. Abst. (Mar. 1979).
56th Amer. Meeting Int. Assoc. Dent. Res. Prog. Abst. (Mar. 1978).

*Primary Examiner*—Douglas W. Robinson

[57] ABSTRACT

Inhibition of bone resorption in mammals suffering from a disease in which bone resorption exceeds new bone formation by administering an $H_1$-blocking antihistamine.

13 Claims, No Drawings

INHIBITION OF BONE RESORPTION WITH $H_1$-BLOCKING ANTIHISTAMINES

The invention described herein was made in the course of work under a grant from the Department of Health, Education, and Welfare.

This application is a continuation-in part-of application Ser. No. 14,070, filed Feb. 22, 1979, now abandoned.

This invention relates to a method for inhibiting bone resorption in mammals by administering an effective amount of $H_1$-blocking antihistamine.

The osteolytic diseases are characterized by rates of bone resorption which are significantly higher than the rates of new bone formation. One disease in which this occurs is chronic destructive periodontal disease (periodontitis); patients suffer gradual erosion of the jaw bone around the roots of the teeth, leading to loosening of the teeth and eventual exfoliation or extraction. Patients suffering from another resorption disease osteoporosis, may experience a loss of bone substance so severe that their bones cannot withstand ordinary mechanical stress, and thus are susceptible to fracture during normal function.

Several methods of treating bone resorption diseases are in use, but none is entirely satisfactory. Known treatments include administering sodium fluoride, calcium compounds, calcitonin, or estrogens.

The method of the present invention can be applied to any mammal suffering from any of the bone resorption diseases characterized by a rate of bone resorption which exceeds the rate of new bone formation. The method comprises administering to a mammal, including a human, suffering from such a disease, an effective amount of any of the $H_1$-blocking antihistamines orally.

$H_1$-blocking antihistamines have been used for a number of years to treat allergic diseases but their therapeutic effectiveness in treating bone diseases has been unknown. However, as disclosed in the present invention, it has been discovered that administering the $H_1$-blocking antihistamines effectively inhibits bone resorption. These agents have the additional advantage of causing minimal and easily avoided side effects. The inhibitory effect of these agents is at present most advantageously demonstrated in tissue culture in which bone resorption has been stimulated by the addition of parathyroid extract. Of the agents herein described, a phenothiazine such as promethazine hydrochloride, which is an $H_1$-blocking antihistamine, is one of the most effective. The phenothiazines which are not $H_1$-blocking antihistamines are not part of the present invention.

Other classes of $H_1$-blocking antihistamines which, according to the method of the present invention, are effective in inhibiting bone resorption include the ethylenediamines, of which tripelennamine hydrochloride and pyrilamine maleate are examples, and the indenes, of which dimethindene maleate is an example.

The following specific example is intended to illustrate more fully the nature of the present invention without acting as a limitation upon its scope.

EXAMPLE

Bone tissue culture systems are prepared according to the method described in Goldhaber, J. Dent. Res. 45:490-499 (1966) and Goldhaber, J. Dent. Res. 50:278-285 (1971). Each tissue sample, in a Leighton tube, is grown in Medium 1, which supports only bone resorption, or in Medium 2, which supports both bone resorption and new bone (osteoid) formation. Medium 1 consists of heated horse serum and Gey's balanced salt solution in the ratio 6:4. In addition, the medium contains 100 units of penicillin, 100 micrograms of streptomycin, 10 units of heparin, and 0.1 units of parathyroid extract per ml of medium. Medium 2 contains heated horse serum, 13-day chicken embryo extract and Gey's balanced salt solution in the ratio 2:2:6, and antibiotics as described above. Water-soluble test compounds are added to the balanced salt solution portion of the media; lipid-soluble compounds are dissolved first in a small amount of absolute ethanol and then added to the complete medium. Each tube receives 2 ml of the appropriate medium and is gassed briefly with a mixture of 50% $O_2$ and 50% $N_2$, stoppered, and placed horizontally in a roller drum at 37° C. Every 2-3 days the used media are replaced with fresh media and the tubes are regassed.

Microscopic observations are made every 2 or 3 days on the living cultures (four tubes per group) and each culture is scored for the extent of bone resorption present. The amount and condition of the cellular outgrowth from the margins of the cultured bone is noted. The used supernatant fluids from cultures maintained in Medium 1 are collected at each "feeding" (2-3 days) and analyzed for calcium content with a Corning Calcium Analyzer, Model 940. Cultures prepared in Medium 1 are maintained for 1 week, whereas those prepared in Medium 2 are maintained for 2 weeks. Upon termination of the experiment, the calvaria are fixed, sectioned, and stained with hematoxylin and eosin. In all experiments, the last score obtained by microscopic observation of each living culture is expressed as the percentage resorption of the total calvarium. These data are averaged per group. Resorption scores determined morphologically correlate to a highly significant degree with the chemical determination of total calcium released into the medium during the course of the experiment. Both sets of data are subjected to statistical evaluation (analysis of variance). Sections of calvaria stained with hematoxylin and eosin are examined for cell viability in all cultures and for the presence of newly formed osteoid in cultures that were maintained in Medium 2.

Table I, column 2 below shows the generic name of the compounds that inhibit bone resorption. Column 3 shows their chemical formulae, whereas columns 4, 5, and 6 show the dose ranges tested in culture, the non-toxic dose ranges inhibiting parathyroid extract-stimulated bone resorption and the selective dose ranges in the remodeling system, respectively. Column 7 shows the adult human oral dose for each compound to achieve inhibition of bone resorption.

TABLE 1

$H_1$-Blocking Antihistamines Inhibitory to Bone Resorption in Tissue Culture

| 1 Class | 2 Generic name | 3 Chemical formula | 4 Dose Range of concentrations tested in tissue culture | 5 Nontoxic dose range inhibiting parathyroid extract-stimulated bone resorption* | 6 Selective dose range in remodeling system** | 7 Daily adult human oral dose |
|---|---|---|---|---|---|---|
| Phenothiazines | Promethazine Hydrochloride | $C_{17}H_{20}N_2S \cdot HCl$ | 1–100 μg/ml | 10–25 μg/ml | 5–25 μg/ml | 25–50 mg/day |
| Ethylenediamines | Tripelennamine Hydrochloride | $C_{16}H_{21}N_3 \cdot HCl$ | 10–50 μg/ml | 20–40 μg/ml | 10–50 μg/ml | |
| | Pyrilamine Maleate | $C_{17}H_{23}N_3O \cdot C_4H_4O_4$ | 10–100 μg/ml | 30–50 μg/ml | 10–100 μg/ml | 25–50 mg up to 4 X/day |
| Indenes | Dimethindene Maleate | $C_{20}H_{24}N_2 \cdot C_4H_4O_4$ | 10–100 μg/ml | 20–50 μg/ml | 10–50 μg/ml | 1–2 mg 1–3 X/day |

*Parathyroid extract (E. Lilly & Co.), 0.1 μ/ml, which usually destroys 60–80% of the calvarium within the 7-day test period.
**Dose range wherein bone resorption is inhibited to a greater extent than new osteoid formation is inhibited over the 14-day test period.

The active agent can be administered in pure form or in the form of its nontoxic acid addition salts or in combination of either of these with any conventional pharmaceutically acceptable nontoxic carrier or vehicle.

What is claimed is:

1. A method for inhibiting bone resorption which comprises administering orally to a mammal suffering from osteoporosis or chronic destructive periodontal disease an $H_1$-blocking antihistamine selected from the group consisting of the $H_1$-blocking phenothiazines, the $H_1$-blocking ethylenediamines, and the $H_1$-blocking indenes, the amount being from 25–50 mg/day in the case of said phenothiazines, 25–50 mg up to 4 times a day in the case of said ethylenediamines, 1–2 mg 1 to 3 times a day in the case of said indenes.

2. The method as claimed in claim 1 in which said $H_1$-blocking phenothiazine is promethazine hydrochloride, said $H_1$-blocking ethylenediamine is selected from the group consisting of tripelennamine hydrochloride and pyrilamine maleate, and said $H_1$-blocking indene is dimethindene maleate.

3. The method as claimed in claim 2 in which said disease is osteoporosis and said antihistamine is promethazine hydrochloride.

4. The method as claimed in claim 2 in which said disease is osteoporosis and said antihistamine is tripelenamine hydrochloride.

5. The method as claimed in claim 2 in which said disease is osteoporosis and said antihistamine is pyrilamine maleate.

6. The method as claimed in claim 2 in which said disease is osteoporosis and said antihistamine is dimethindene maleate.

7. The method as claimed in claim 2 in which said disease is periodontitis and said antihistamine is promethazine hydrochloride.

8. The method as claimed in claim 2 in which said disease is periodontitis and said antihistamine is tripellenamine hydrochloride.

9. The method as claimed in claim 2 in which said disease is periodontitis and said antihistamine is pyrilamine maleate.

10. The method as claimed in claim 2 in which said disease is periodontitis and said antihistamine is dimethindene maleate.

11. The method as claimed in claim 1 in which said $H_1$-blocking antihistamine is an $H_1$-blocking phenothiazine.

12. The method as claimed in claim 1 in which said $H_1$-blocking antihistamine is an $H_1$-blocking ethylenediamine.

13. The method as claimed in claim 1 in which said $H_1$-blocking antihistamine is an $H_1$-blocking indene.

* * * * *